(12) United States Patent
Goleti Venkata et al.

(10) Patent No.: US 10,485,496 B2
(45) Date of Patent: Nov. 26, 2019

(54) RADIOTHERAPY APPARATUS WITH ON-BOARD STEREOTACTIC IMAGING SYSTEM

(71) Applicant: PANACEA MEDICAL TECHNOLOGIES PVT. LTD, Whitefield Bangalore (IN)

(72) Inventors: Subrahmanyam Goleti Venkata, Whitefield Bangalore (IN); Avinash Rao Kuppa, Whitefield Bangalore (IN); Deepak Fernando Savarinathan, Whitefield Bangalore (IN)

(73) Assignee: Panacea Medical Technologies, Pvt., Ltd., Bangalore (IN)

(*) Notice: Subject to any disclaimer, the term of this patent is extended or adjusted under 35 U.S.C. 154(b) by 284 days.

(21) Appl. No.: 15/506,329

(22) PCT Filed: Apr. 14, 2015

(86) PCT No.: PCT/IB2015/052701
§ 371 (c)(1),
(2) Date: Feb. 24, 2017

(87) PCT Pub. No.: WO2016/030772
PCT Pub. Date: Mar. 3, 2016

(65) Prior Publication Data
US 2017/0231583 A1    Aug. 17, 2017

(30) Foreign Application Priority Data
Aug. 25, 2014    (IN) .......................... 4150/CHE/2014

(51) Int. Cl.
*A61B 6/03*    (2006.01)
*A61N 5/10*    (2006.01)
(Continued)

(52) U.S. Cl.
CPC ............ *A61B 6/4014* (2013.01); *A61B 6/032* (2013.01); *A61B 6/4085* (2013.01);
(Continued)

(58) Field of Classification Search
CPC ......... A61B 6/03; A61B 6/032; A61B 6/4014; A61B 6/4085; A61B 6/4266; A61B 6/486;
(Continued)

(56) References Cited

U.S. PATENT DOCUMENTS 8,536,547 B2    9/2013    Maurer
2009/0161816 A1    6/2009    De Man
(Continued)

FOREIGN PATENT DOCUMENTS

WO    2014047518 A1    3/2014

OTHER PUBLICATIONS

Sun, M et al., "Correction for patient table-induced scattered radiation in cone-beam computed 1-6 tomography (CBCT)". Mar. 22, 2011. Med. Phys. 38 (4), Apr. 2011, pp. 2058-2073 [online], [retrieved on Aug. 3, 2015). Retrieved from the internet <URL:http://scitation.aip.org/content/aapm/journal/medphys/38/4/10.1118/1.3557468>; p. 2060, section 11.A.2; Table I.

*Primary Examiner* — Mark R Gaworecki
(74) *Attorney, Agent, or Firm* — J. Peter Paredes; Rosenbaum IP, P.C.

(57) ABSTRACT

The present invention provides a radiotherapy apparatus (100) to generate both photon and electron beam mounted with dual KV beam ray source used for stereotactic imaging and CBCT (Cone Beam Computed Tomography) image with a greater FOV (Field Of View). The apparatus (IOO) comprises of a ring gantry (101), which includes at least two KV sources (102a and 102b), at least two movable detector (103 and 104) and a LINAC X-ray tube (106). The two
(Continued)

movable detectors (103, 104) include a first movable detector (104) and a second movable detector (103). The second movable detector (103) has mechanism capture a half fan mode of X-ray beam of imaging radiation with a greater FOV having 250×450 mm. The half fan mode of X ray is captured by moving the second movable detector (103) or first movable detector (104) further towards the ISO centre (105) of the ring gantry (101).

3 Claims, 2 Drawing Sheets

(51) Int. Cl.
*G01N 23/04* (2018.01)
*A61B 6/00* (2006.01)
*G01N 23/046* (2018.01)

(52) U.S. Cl.
CPC .......... *A61B 6/4266* (2013.01); *A61N 5/1049* (2013.01); *A61N 5/1081* (2013.01); *A61N 2005/1061* (2013.01); *A61N 2005/1089* (2013.01); *G01N 23/046* (2013.01)

(58) Field of Classification Search
CPC ..... A61B 6/5235; A61B 6/5258; A61B 6/542; A61N 5/1049; A61N 5/1081; A61N 2005/1061; A61N 2005/1089; G01N 23/046; G01N 2223/1006; G01N 2223/102; G01N 2223/414
See application file for complete search history.

(56) References Cited

U.S. PATENT DOCUMENTS

2010/0195804 A1  8/2010  Dafni
2012/0236982 A1  9/2012  Star-Lack

RADIOTHERAPY APPARATUS WITH ON-BOARD STEREOTACTIC IMAGING SYSTEM

TECHNICAL FIELD OF THE INVENTION

The present invention relates to a radiotherapy apparatus mounted on a ring gantry to generate photons and electron beams. This apparatus is equipped with stereotactic imaging system which uses two sets of KV X-ray beam and a detector mounted isocentric to the gantry motion to take stereotactic images and CBCT (Cone Beam Computed Tomography) image with a greater FOV (Field Of View).

BACKGROUND OF THE INVENTION

Radiotherapy is the application of high-energy ionizing radiation to treat diseases and abnormal tissues in patients. Typically, the radiation is collimated into a beam and directed towards a target area for treatment. A high enough radiation doses will kills the targeted cells. Radiotherapy is typically characterized by a low dose per fraction (e.g., 100-200 centigray), shorter fraction times (e.g., 10 to 30 minutes per treatment) and hyper-fractionation (e.g., 30 to 45 fractions). A ring gantry-based system tends to exhibit relatively high mechanical stability, i.e., less of the deformation problems, and thus can reproducibly and accurately position the radiation source. The ring gantry having radiotherapy apparatus generates stereotactic images and CBCT (Cone Beam Computed Tomography) image. These are the diagnostic tools for providing a type 3-D volumetric image with considerable prospects.

Various types of conventional ring gantries are known in the prior art, wherein most of them typically include dual KV sources and dual flat panel detectors to generate CBCT image and stereotactic image. In the existing U.S. Pat. No. 8,536,547, it is proposed for the creation of CBCT image using a first imaging source and a first imaging detector in the ring gantry. The imaging detectors are fixably mounted in the inner periphery of the ring gantry. In this invention, the produced or captured CBCT image does not provide a greater FOV (Field Of View) with respect to the patient plane.

Typically, the radiotherapy machines which use dual detectors and dual KV image source for stereotactic imaging are not capable of taking a CBCT image with half fan mode and hence they cannot produce a CBCT for higher field of view (greater than 250×250 mm). In order to generate CBCT image with FOV greater than 250×250 mm, there is need of a different machine which has a feasibility to take a CBCT image for larger volumes. In conventional radiotherapy machines with ring gantry, there is no electron mode and customers have to depend on other machines to deliver electron therapy.

Hence, there is need of an apparatus which includes single ring gantry machine to generate both photon beam and electron beam and an imaging system which can generate both CBCT image with greater FOV and stereotactic imaging which is simple and durable.

SUMMARY OF THE INVENTION

The present invention overcomes the drawbacks in the prior art and provides a radiotherapy apparatus to generate to CBCT (Cone Beam Computed Tomography) with a greater Field Of View (FOV) with a wider bore in the gantry for the patient. The apparatus comprises of a ring gantry which includes at least two KV sources, at least two detectors and a LINAC (Linear Accelerator) X-ray tube. The ring gantry has a wider (greater than 700 mm) central opening to accommodate the body of a patient positioned along the longitudinal axis and extending there through. The two KV sources in the ring gantry are used for generating a beam of imaging radiation, which is directed towards the patient table. The two detectors are arranged in the ring gantry to detect the beam of imaging radiation after it has passed through the patient table, wherein the two detectors have a mechanism to generate the beam of imaging data with a greater FOV. The two detectors are the first detector and the second detector. The first detector has mechanism to generate a full fan mode of X-ray beam of imaging radiation with a FOV of at least 250×250 mm, wherein the full fan mode of X ray is generated by moving the first detector close to the patient's plane. The second detector has mechanism to generate a half fan mode of X-ray beam of imaging radiation with a greater FOV having 250×450 mm, wherein the half fan mode of X-ray is generated by moving the second detector further towards the ISO centre of the ring gantry. These two detectors when placed on the inner periphery of the gantry are used for capturing stereotactic images.

In the preferred embodiment, the beam of imaging radiation is said to be CBCT (Cone Beam Computed Tomography) imaging and stereotactic imaging.

According to another embodiment, the half fan mode of X-ray beam of imaging radiation is generated by moving the first detector further towards the ISO centre.

According to another embodiment, the apparatus further comprises of a LINAC (Linear Accelerator) X-ray tube mounted on the ring gantry to produce electron beam along with photon beam for electron therapy.

The invented apparatus eliminates the need of radiotherapy machine which does not generate an electron beam and a stereotactic imaging system which cannot generate and CBCT image with FOV greater than 250×250 mm. The invented apparatus provides a single ring gantry radiotherapy machine with two sets of KV source and detector, wherein the detectors are having mechanism which are capable of capturing stereotactic images and CBCT image with a greater FOV having 250×450 mm. The invented apparatus is more suitable for applications in SRS, SBRT and normal radiotherapy, scanning device, hospitals, diagnostic centers etc.

The present invention generates CBCT image with half fan mode of X-ray beam and full fan mode of X-ray beam with coverage of 250×450 mm at ISO center and a stereotactic image using only two sets of detector and KV beam source. This allows treating both with Flattening filter and flattening filter free method. The invented single ring gantry radiotherapy machine has a mechanism to deliver both photons and electrons.

It is to be understood that both the foregoing general description and the following details description are exemplary and explanatory and are intended to provide further explanation of the invention as claimed.

BRIEF DESCRIPTION OF THE DRAWINGS

The foregoing and other features of embodiments will become more apparent from the following detailed description of embodiments when read in conjunction with the accompanying drawings. In the drawings, like reference numerals refer to like elements.

DETAILED DESCRIPTION OF THE INVENTION

Reference will now be made in detail to the description of the present subject matter, one or more examples of which are shown in figures. Each embodiment is provided to explain the subject matter and not a limitation. These embodiments are described in sufficient detail to enable a person skilled in the art to practice the invention, and it is to be understood that other embodiments may be utilized and that logical, physical, and other changes may be made within the scope of the embodiments. The following detailed description is, therefore, not be taken as limiting the scope of the invention, but instead the invention is to be defined by the appended claims.

The present invention provides a radiotherapy apparatus to generate both photon beam and electron beam mounted with dual KV beam X-ray source used for stereotactic imaging and CBCT (Cone Beam Computed Tomography) image with a greater FOV (Field Of View). The apparatus comprises of a ring gantry, wherein the ring gantry includes at least two KV source, a two movable detector and a LINAC X-ray tube. The two movable detectors include a first movable detector and a second movable detector. The first movable detector has mechanism to capture a full fan mode of X-ray beam of imaging radiation with a FOV of at least 250×250 mm. The second movable detector has mechanism to capture a half fan mode of X-ray beam of imaging radiation with a greater FOV having 250×450 mm. The half fan mode of X ray is generated by moving the second movable detector or first movable detector further towards the ISO centre of the ring gantry. The present invention generates CBCT image with half fan mode of X-ray beam and full fan mode of X-ray beam with coverage of 250×450 mm at ISO center and a stereotactic image using only two sets of detector and KV beam source. This allows treating both with Flattening filter and flattening filter free method. The invented single ring gantry radiotherapy machine has a mechanism to deliver both photons and electrons.

Figure 1:
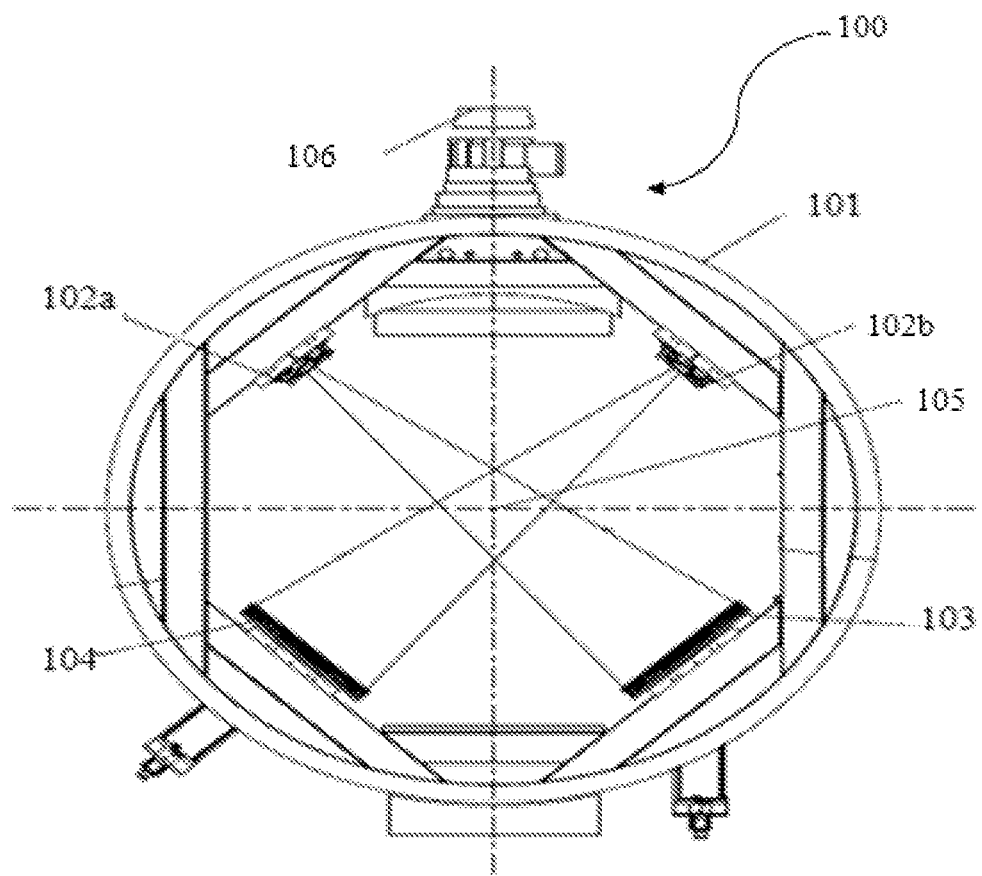
FIG. 1 illustrates a perspective view of a ring gantry having two sets of KV source and detectors placed a part on the periphery of the inner ring to accommodate a wider opening in the gantry (more than 700 mm) for taking stereotactic imaging, according to one embodiment of the invention.

FIG. 1 illustrates a perspective view of a ring gantry having two sets of KV source and detectors placed a part on the periphery of the inner ring to accommodate a wider opening in the gantry (more than 700 mm) for taking stereotactic imaging, according to one embodiment of the invention. The apparatus (100) comprises of a ring gantry (101) which includes a two KV source (102a and 102b), at least two movable detectors (103 and 104) and a LINAC X-ray tube (106). The ring gantry has a wide central opening (more than 700 mm) to accommodate the body of a patient positioned along a longitudinal axis and extending there through. The ring gantry (101) includes the two KV sources (102a and 102b) for generating a beam of imaging radiation, which are directed towards the patient table. The two movable detectors (103 and 104) are arranged in the ring gantry (101) to detect the beam of imaging radiation after it has passed through the patient's table. The two movable detectors (103 and 104) have a mechanism to capture the beam of imaging data with greater FOV. The two movable detectors (103 and 104) are a first movable detector (104) and a second movable detector (103). The first movable detector (104) has mechanism to capture a full fan mode of X-ray beam (107) of imaging radiation with a FOV of at least 250×250 mm. The full fan mode of X-ray beam (107) is generated by moving the first movable detector (104) close to the patient's plane. The second movable detector (103) has mechanism to capture a half fan mode of X-ray beam (108) of imaging radiation with a greater FOV having 250×450 mm. The half fan mode of X-ray beam (108) is captured by moving the second movable detector (103) further towards the ISO centre (105) of the ring gantry. The half fan mode of X-ray beam (108) of imaging radiation is also captured by moving the first movable detector (104) further towards the ISO centre (105).

The first movable detector (104) and the second movable detector (103) are mounted ISO centrically (105) on the ring gantry which are 90 degree or at a defined angle apart from each other. The beam of imaging radiation is said to be used for CBCT (Cone Beam Computed Tomography) imaging and stereotactic imaging.

The apparatus further comprises of a LINAC (Linear Accelerator) X-ray tube (106) mounted on the ring gantry (101) to produce electron beams along with photon beams for electron therapy. The electron beams are produced by keeping the movable target close to the LINAC X-ray tube (106) such that electron beam coming out of the LINAC X-ray tube (106) is hit on a scattering foil to generate electron beams for electron therapy.

Figure 2:
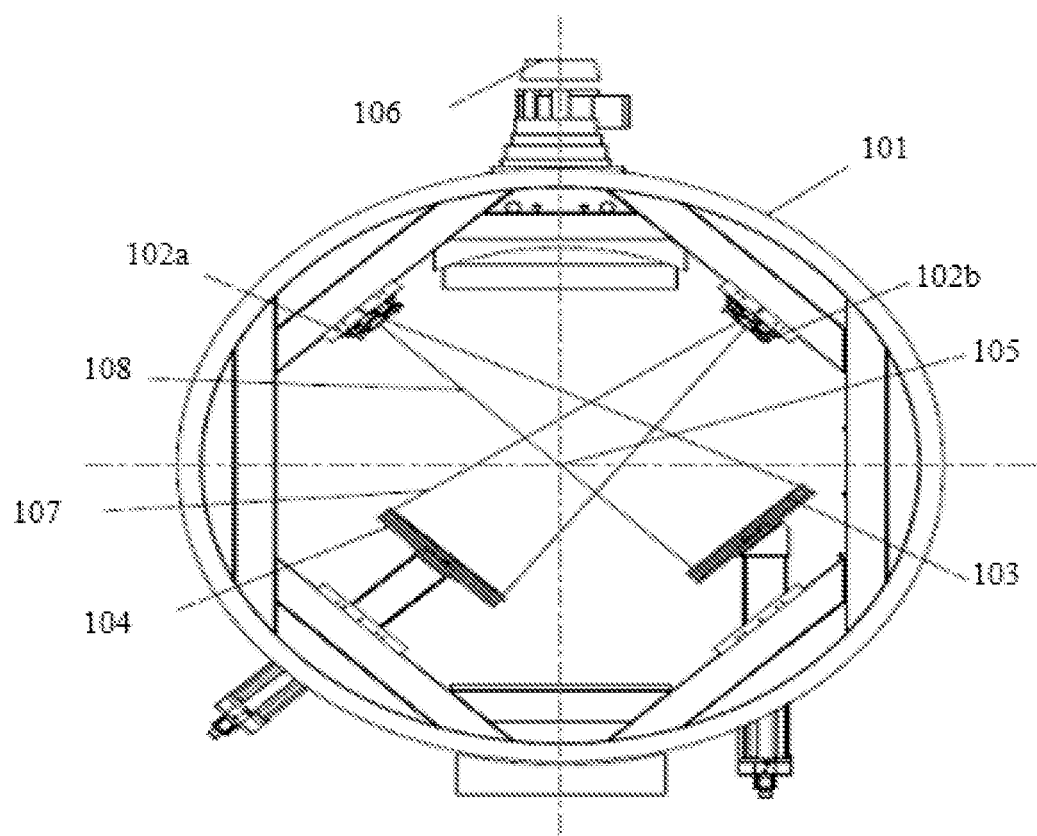
FIG. 2 illustrates a perspective view of the ring gantry having two sets of KV source and detectors with its new position for capturing CBCT images in both half fan mode and full fan mode, according to one embodiment of the invention.

FIG. 2 illustrates a perspective view of the ring gantry having two sets of KV source and detectors with its new position for capturing half fan mode and full fan mode, according to one embodiment of the invention. The ring gantry (101) generates a CBCT image with half fan mode of X-ray and full fan mode of X-ray with coverage of 250×450 mm at ISO center (105) and a stereotactic image using only two movable detectors (103 and 104) and two KV beam source (102a and 102b). The first movable detector (104) has mechanism to capture a full fan mode of X-ray beam (107) of imaging radiation with a FOV of at least 250×250 mm. The full fan mode of X-ray beam (107) is captured by moving the first movable detector (104) close to the patient's plane. The second movable detector (103) has mechanism to capture a half fan mode of X-ray beam (108) of imaging radiation with a greater FOV having 250×450 mm. The half fan mode of X ray (108) is captured by moving the second movable detector (103) further towards the ISO centre (105) of the ring gantry.

The invented apparatus eliminates the need of radiotherapy machine which does not generate an electron beam and a stereotactic imaging system which cannot generate and CBCT image with FOV greater than 250×250 mm. The invented apparatus provides a single ring gantry radiotherapy machine with two sets of KV source and detector, wherein the detectors are having mechanism which are capable of capturing stereotactic images and CBCT image with a greater FOV having 250×450 mm. The invented apparatus is more suitable for applications in SRS, SBRT and normal radiotherapy, scanning device, hospitals, diagnostic centers etc.

It is to be understood, however, that even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

We claim:

1. A radiotherapy apparatus (100) for generating electron beam and CBCT (Cone Beam Computed Tomography) image with a wide FOV (Field Of View), wherein the apparatus (100) comprises of:
   a) a ring gantry (101), having a central opening to accommodate the body of a patient on a patient table positioned along a longitudinal axis of the ring gantry (101) and extending there through;
   b) at least two KV beam X-ray sources (102a and 102b), placed on the periphery of an inner ring in the ring gantry (101) for generating a beam of imaging radiation directed towards the patient's table for stereotactic imaging;
   c) at least two movable detectors (103 and 104) which are placed in the ring gantry (101) mounted iso-centrically on the ring gantry and separated by an angle of 90 degrees, for detecting the beam of imaging radiation after it has passed through the patient table;
   d) an iso-centre (105) at which the vertical tilt axis of the gantry (101) intersects the longitudinal axis of the gantry (101);
   e) the at least two movable detectors (103 and 104) are a first movable detector (104) and a second movable detector (103), wherein
      i) the first movable detector (104) captures a full fan mode of X-ray beam (107) of imaging radiation having FOV of at-least 250×250 mm by moving the first movable detector (104) closer to the plane of the patient;
      ii) the second movable detector (103) captures a half fan mode of X-ray beam (108) of imaging radiation having FOV of at least 250×450 mm by moving the second movable detector (103) further towards the iso-centre (105) of the ring gantry; and
   f) a LINAC (Linear Accelerator) X-ray tube (106) mounted on the ring gantry (101) for producing electron beams and photon beams.

2. The apparatus (100) as claimed in claim 1, wherein the half fan mode of X-ray beam (108) of imaging radiation is generated by moving the first movable detector (104) further towards the iso-centre (105).

3. The apparatus (100) as claimed in claim 1, wherein a beam of imaging radiation comprising photon beam and X-ray beams captured and detected by the movable detectors (103 and 104) are used in CBCT (Cone Beam Computed Tomography) imaging and stereotactic imaging.

* * * * *